US006937014B2

(12) United States Patent
Sun et al.

(10) Patent No.: US 6,937,014 B2
(45) Date of Patent: Aug. 30, 2005

(54) METHOD FOR OBTAINING MULTI-DIMENSIONAL PROTON DENSITY DISTRIBUTIONS FROM A SYSTEM OF NUCLEAR SPINS

(75) Inventors: Boqin Sun, Concord, CA (US); Keh-Jim Dunn, San Ramon, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 10/396,941

(22) Filed: Mar. 24, 2003

(65) Prior Publication Data

US 2004/0189296 A1 Sep. 30, 2004

(51) Int. Cl.[7] .......................... G01V 3/00; G01R 33/20
(52) U.S. Cl. ...................... 324/303; 324/306; 324/307; 324/300
(58) Field of Search ................ 324/303, 306, 324/309, 300–322; 600/407–434

(56) References Cited

U.S. PATENT DOCUMENTS

| | | |
|---|---|---|
| 4,710,713 A | 12/1987 | Strikman |
| 4,717,876 A | 1/1988 | Masi et al. |
| 4,717,877 A | 1/1988 | Taicher et al. |
| 4,717,878 A | 1/1988 | Taicher et al. |
| 5,023,551 A | 6/1991 | Kleinberg et al. |
| 5,055,787 A | 10/1991 | Kleinberg et al. |
| 5,055,788 A | 10/1991 | Kleinberg et al. |
| 5,212,447 A | 5/1993 | Paltiel |
| 5,280,243 A | 1/1994 | Miller |
| 5,291,137 A | 3/1994 | Freedman |
| 5,309,098 A | 5/1994 | Coates et al. |
| 5,363,041 A | 11/1994 | Sezginer |
| 5,381,092 A | 1/1995 | Freedman |
| 5,412,320 A | 5/1995 | Coates |
| 5,486,762 A | 1/1996 | Freedman et al. |
| 5,517,115 A | 5/1996 | Prammer |
| 5,557,200 A | 9/1996 | Coates |
| 5,585,720 A | 12/1996 | Edwards |

(Continued)

FOREIGN PATENT DOCUMENTS

WO      WO 01/42817 A1    6/2001

OTHER PUBLICATIONS

English, A.E., Whittall, K.P. Joy, M.L.G., and Henkelman, R.M., Quantitative Two–Dimensional Time Correlation Relaxometry, Magnetic Resonance in Medicine, 22, 425–434, 1991.

(Continued)

Primary Examiner—Diego Gutierrez
Assistant Examiner—Tiffany A. Fetzner
(74) Attorney, Agent, or Firm—Richard J. Schulte

(57) ABSTRACT

The present invention provides a method for obtaining a multi-dimensional proton density distribution from a system of nuclear spins. A plurality of nuclear magnetic resonance (NMR) data is acquired from a fluid containing porous medium having a system of nuclear spins. A multi-dimensional inversion is performed on the plurality of nuclear magnetic resonance data using an inversion algorithm to solve a mathematical problem employing a single composite kernel to arrive at a multi-dimensional proton density distribution. Ideally, the mathematical problem can be cast in the form of a Fredholm integral of the first kind wherein a two or more kernels can be reduced to a single composite kernel for ease of solution. Preferably, a series of conventional CPMG pulse sequences, using a conventional NMR tool, can be used to excite the system of nuclear spins. The present invention further includes a regression method which reduces computational efforts by retaining only those grid points, and preferably their neighboring grid points, which have non-zero values, during subsequent iterations of solving for the multi-dimensional proton density distribution. This regression process can be repeated until the density distribution is satisfactorily smooth.

21 Claims, 7 Drawing Sheets

U.S. PATENT DOCUMENTS

| | | | |
|---|---|---|---|
| 5,680,043 | A | 10/1997 | Hurlimann et al. |
| 5,696,448 | A | 12/1997 | Coates et al. |
| 5,796,252 | A | 8/1998 | Kleinberg et al. |
| 5,936,405 | A | 8/1999 | Prammer et al. |
| 6,005,389 | A | 12/1999 | Prammer |
| 6,049,205 | A | 4/2000 | Taicher et al. |
| 6,069,477 | A | 5/2000 | Chen et al. |
| 6,133,735 | A | 10/2000 | Hurlimann et al. |
| 6,147,489 | A | 11/2000 | Freedman et al. |
| 6,166,543 | A | 12/2000 | Sezginer et al. |
| 6,255,818 | B1 | 7/2001 | Heaton et al. |
| 6,316,940 | B1 | 11/2001 | Akkurt |
| 6,344,744 | B2 | 2/2002 | Taicher et al. |
| 6,366,087 | B1 | 4/2002 | Coates et al. |
| 6,369,567 | B1 | 4/2002 | Song et al. |
| 6,462,542 | B1 * | 10/2002 | Venkataramanan et al. . 324/303 |
| 6,522,136 | B1 | 2/2003 | Hurlimann et al. |
| 6,559,639 | B2 | 5/2003 | Minh et al. |
| 6,570,382 | B1 | 5/2003 | Hurlimann et al. |
| 6,573,715 | B2 | 6/2003 | King et al. |
| 6,577,125 | B2 | 6/2003 | Prammer et al. |
| 6,597,171 | B2 * | 7/2003 | Hurlimann et al. ......... 324/303 |
| 2002/0067164 | A1 | 6/2002 | Venkataramanan et al. |
| 2002/0105326 | A1 | 8/2002 | Hunlmann et al. |
| 2004/0189296 | A1 * | 9/2004 | Sun et al. .................... 324/306 |

OTHER PUBLICATIONS

Lee, J–H., Labadie, C. Springer, C.S., and Harbison, G.S., Two Dimensional Inverse Laplace Transform NMR. Altered Relaxation Times Allow Detection of Exchange Correlation, J. Am. Chem. Soc., 115, 7761–7764, 1993.

Akkurt, R., Vinegar, H.J., Tutunjian, P.N., and Guillory, A.J., NMR Logging of Natural Gas Reservoirs, The Log Analyst, 33–42, Nov.–Dec. 1996.

Dunn, K–J. and Latorraca, G.A., The Inversion of NMR Log Data Sets With Different Measurement Errors, Journal of Magnetic Resonance, 140 153–161, 1999.

Chen, S., Georgi, D.T., Withjack, E.M., Minetto, C., Olima, O., and Gamin, H., Estimation of Oil Viscosity With Multiple TE Dual Wait–Time MRIL Logs, Petrophysics. vol. 41, No. 1, 33–39, Jan.–Feb. 2000.

Freedman, R., Sezginer, A., Flaum, M., Matteson, A, Lo, S., and Hirasaki, G.J., A New NMR Method of Fluid Characterization in Reservoir Rocks: Experimental Confirmation and Simulation Results, Society of Petroleum Engineers (SPE Paper 63214), 1–15, 2000.

Dunn, K–J., Appel, M. Freeman, J.J., Gardner, J.S., Hirasaki, G.J., Shafer, J.L., and Zhang, G., Interpretation of Restricted Diffusion and Internal Field Gradients in Rock Data. Published in the Proceedings of $42^{nd}$ Annual Symposium of Society of Professional Well Log Analysts. Houston, TX, Paper AAA, 1–12, 2001.

Venkataramanan, L., Song, Y.Q., and Hürlimann, M.D., Solving Fredholm Integrals of the First Kind With Tensor Product Structure in 2 and 2.5 Dimensions, IEEE Transactions on Signal Processing, vol. 50, No. 5, 1017–1026, May 2002.

Hurlimann, M.D., Venkataramanan, L., Flaum, C., Speir, P. Karmonik, C., Freedman, R., and Heaton, N., Diffusion–Editing: New NMR Measurement of Saturation and Pore Geometry, SPWLA $43^{rd}$ Annual Logging Symposium, Paper FFF, 1–14, Jun. 2–5, 2002.

Dunn, K–J., Enhanced Transverse Relaxation in Porous Media Due to Internal Field Gradients, Journal of Magnetic Resonance 156, 1–10, 2003.

Hurlimann, M.D., and Venkataramanan, L., Quantitative Measurement of Two–Dimensional Distribution Functions of Diffusion and Relaxation in Grossly Inhomogeneous Fields. Journal of Magnetic Resonance 157, 31–42, 2002.

Sun, B and Dunn, K–J, Probing the Internal Field Gradients of Porous Media. The American Physical Society, Physical Review E. Vol. 65, 051309, 1–7, 2002.

* cited by examiner

METHOD FOR OBTAINING MULTI-DIMENSIONAL PROTON DENSITY DISTRIBUTIONS FROM A SYSTEM OF NUCLEAR SPINS

TECHNICAL FIELD

The present invention relates generally to nuclear magnetic resonance (NMR) analysis of properties of fluid saturated porous media, including rock samples containing hydrocarbons, and more particularly, to methods of analyzing NMR data to determine multi-dimensional distributions of those properties.

BACKGROUND OF THE INVENTION

Nuclear magnetic resonance technology has been widely used to measure petrophysical properties of fluid containing porous media. Examples of such petrophysical properties include pore size, surface-to-volume ratio, formation permeability, and capillary pressure. In determining these properties, longitudinal relaxation time $T_1$ and transverse relaxation time $T_2$ are often of interest. Relaxation time is the time associated with nuclear spins to return to their equilibrium positions after excitation. The longitudinal relaxation time $T_1$ relates to the alignment of spins with an external static magnetic field. Transverse relaxation time $T_2$ is a time constant that identifies the loss of phase coherence that occurs among spins oriented to an angle to the main magnetic field. This loss is caused, in part, by the interactions between spins.

NMR log measurements can be performed using, for example, a centralized MRIL.RTM. tool made by NUMAR, a Halliburton company, or a sidewall CMR tool made by Schlumberger. The MRIL.RTM. tool is described, for example, in U.S. Pat. No. 4,710,713 to Taicher et al. Details of the structure and the use of the MRIL.RTM. tool, as well as the interpretation of various measurement parameters are also discussed in U.S. Pat. Nos. 4,717,876; 4,717,877; 4,717,878; 5,212,447; 5,280,243; 5,309,098; 5,412,320; 5,517,115, 5,557,200 and 5,696,448. A Schlumberger CMR tool is described, for example, in U.S. Pat. Nos. 5,055,787 and 5,055,788 to Kleinberg et al. U.S. Pat. No. 5,023,551 generally describes the use of NMR well logging. The content of the above patents is hereby expressly incorporated by reference.

The $T_2$ distributions of brine-saturated rocks often reflect partial porosities of different pore sizes. The sum of the $T_2$ amplitudes at different relaxation times, when properly calibrated, is equal to the total porosity. The amplitude of each relaxation time is equal to the partial porosity of that particular $T_2$ relaxation time, and is related to a particular pore size.

When multiple pore fluids, such as oil, gas, and water, are present, it becomes somewhat difficult to differentiate them from their NMR signals especially when their $T_2$ signals overlap. Methods have been proposed in the past to determine the type and quantity of the hydrocarbons contained in the pore space of rocks such as those described by Akkurt, R., Vinegar, H. J., Tutunjian, P. N., and Guillory, A. J., The Log Analyst, 37, 33 (1996). These methods use either different echo spacings, or different wait times, or combinations thereof, for Carr-Purcell-Meiboom-Gill (CPMG) pulse sequences to obtain shifts or differences of $T_2$ distributions for hydrocarbon identification and quantification, and sometimes for oil viscosity determination.

More elaborate methods, Chen, S., Georgi, D. T., Withjack, E. M., Minetto, C., Olima, O., and Gamin, H., Petrophysics, 41, 33 (2000) and Freedman, R., Sezginer, A., Flaum, M., Matteson, A., Lo, S., and Hirasaki, G. J., SPE Paper 63214, Society of Petroleum Engineers, Dallas, Tex. (2000), try to solve problems by analyzing the data analytically, or inverting data with different echo spacings and wait times simultaneously. But the successful applications of these methods heavily rely on the knowledge of the diffusion coefficients D of the unknown fluids. Whenever the $T_2$ signals are insensitive to such manipulations, the result of such analysis becomes ambiguous and is sometimes inherently difficult such as when the $T_2$ signal of the oil overlaps with that of irreducible water. The inversion algorithm is cast in a framework of a one-dimensional relaxation time distribution. The resulting data information is obtained and displayed in a one-dimension plot, i.e., the proton population as a function of $T_2$ relaxation times. Further, information regarding internal field gradients within rocks cannot be readily extracted with regular CPMG pulse sequences to provide a full description of distributions of internal field gradients as a function of pore sizes.

Recently, it has been proposed by Hurlimann, M. D., Venkataramanan, L., Flaum, C., Speir, P., Karmonik, C., Freedman, R., and Heaton, N., "Diffusion Editing: New NMR Measurement of Saturation and Pore Geometry", SPWLA Proc. 43$^{rd}$ Annual Logging Symposium, Oiso, Japan, Paper FFF (2002), that two-window type modified CPMG pulse sequences be used to acquire echo trains in magnetic field gradients thereby facilitating the acquisition of a 2D NMR proton distribution by the subsequent data inversion. Along with requiring special pulses sequences, the inversion algorithm requires two separable kernels to obtain the 2D NMR proton distribution. See U.S. patent applications 20020104326 and 20020067164, the contents of which are hereby incorporated by reference in their entirety. A related method has been reported by Sun, B. and Dunn, K-J., "Probing the internal field gradients in porous media", Phys. Rev. E 65:051309 (2002). Unfortunately, these methods require significant modifications to current conventional logging tools to produce the desired two-window type modified CPMG pulse sequences. Also, the inversion algorithm requires the two kernels to be separable.

Regular CPMG Pulses and Echo Trains

A regular CPMG pulse sequence includes a 90 degree pulse followed by a series of 180 degree pulses, as seen in FIGS. 1A and 1B, and comports with the following expression:

$$\left(\frac{\pi}{2}\right)_{\pm x} [-\tau_k - \pi_y - \tau_k - acq-]_{n_k}$$

where $$\left(\frac{\pi}{2}\right)$$

is 90 degree pulse applied along the plus and minus x-axis with respect to a reference in the rotating frame;

$\tau_k$ is half of the echo spacing $TE_k$ of the k-th echo train;

$\pi_y$ is a 180 degree pulse applied along y axis in the rotating frame;

acq represents an acquisition of an echo;

$n_k$ is the number of echoes in the k-th echo train.

Accompanying the regular CPMG pulse sequence is an external magnetic field gradient $G_k$ and an optional pulse gradient applied between 180 degree RF pulses. The width of the pulse field gradient is $\delta_k$ and the separation between successive gradient pulses is $\Delta_k$. Meanwhile the system of nuclear spins is also subjected to the internal field gradient caused by the external magnetic field and susceptibility contrast between grains and pore fluids. In the following a symbol g represents the total magnetic field gradient to which the system of nuclear spins is subjected.

The echo train of a regular CPMG pulse sequence has the following form relating the echo amplitude $b_i$ to the $T_2$ relaxation time:

$$b_i = \sum_{j=1}^{m} a_j \exp(-t_i/T_{2j}) + \varepsilon_i, \quad i = 1, \ldots, n, \quad t_i = iTE, \quad (1)$$
$$j = 1, \ldots, m$$

where $b_i$ is the i-th echo amplitude, $\varepsilon_i$ is noise, TE is the time between echoes, $t_i$ is the decay time, n is the number echoes collected, m is the number of relaxation times equally spaced on a logarithmic scale assumed for the model, and $a_j$ is the $T_2$ amplitude associated with the relaxation time $T_{2j}$ to be solved by an inversion.

Eq. (1) is the simplest form for a regular CPMG echo train, where it is assumed that either the magnetic field is homogeneous or the TE is small enough that the diffusion effect is negligible. The polarization factor, $1-\exp(-WT/T_{1j})$ is ignored, where WT is the wait time between two excitations of the CPMG pulse sequences, and $T_{1j}$ are $T_1$ relaxation times often chosen to be equally spaced on a logarithmic scale similar to that of $T_2$.

This polarization factor can always be added back to the equation when full polarization is not achieved.

Eq. (1), when cast in integral form, is a Fredholm integral of the first kind as shown in the following expression:

$$b(t) = \int a(T_2) k_1(t, T_2) dT_2 + \varepsilon, \quad (2)$$

where $k_1(t, T_2) = \exp(-t/T_2)$ is the kernel and $a(T_2)$ is the amplitude associated with the variable $T_2$ to be solved.

When a rock sample or formation is in a magnetic field gradient and large echo spacing is being used, Eq. (1) becomes:

$$b_i = \sum_{j=1}^{m} a_j \exp\left(-\frac{1}{12}\gamma^2 g^2 TE^2 D t_i\right) \exp(-t_i/T_{2j}) + \varepsilon_i \quad (3)$$

where $\gamma$ is the gyromagnetic ratio, g is the magnetic field gradient, and D is the diffusion coefficient of the pore fluid. If there are multiple fluids in the pore space with different diffusion coefficients, and/or there is a distribution of magnetic field gradient where g is simply a selected averaged value, then, as a result, there will be a distribution of the diffusion coefficient D, and Eq.(3) can be written as:

$$b_{ik} = \sum_{j=1}^{m}\sum_{l=1}^{p} a_j c_l \exp\left(-\frac{1}{12}\gamma^2 g^2 TE_k^2 D_l t_i\right) \exp(-t_i/T_{2j}) + \varepsilon_{ik} \quad (4)$$

where the distribution of D is indicated by the index I, and the amplitude of the distribution, $c_l$, satisfies the following condition:

$$\sum_{l=1}^{p} c_l = 1 \quad (5)$$

and p is the number of diffusion coefficients equally spaced on a logarithmic scale chosen for the model. Note there is an extra index k in $b_{ik}$ and $\varepsilon_{ik}$ indicating that the echo train was taken with a specific echo spacing $TE_k$.

To cast Eq. (4) in the form of a Fredholm integral, the following expression may be used:

$$b(t, TE) = \int a(T_2) c(D) k_2(t, TE, D) k_1(t, T_2) dD dT_2 + \varepsilon, \quad (6)$$

where $k_2(t, TE, D)$ is the second kernel which describes the diffusion effect in the gradient field. It is observed that the two kernels tangle together because of the common variable t. As indicated above, one prior approach to overcome this entanglement is to separate these two kernels by fixing the variable t in the second kernel using a two-window type modified CPMG pulse sequences. FIGS. 2A and 2B illustrate examples of these types of two-window pulse sequences. Usually, the first window of this type of modified CPMG pulse sequences has a window length, $t_d$, which fixes the t in $k_2(t, TE, D)$. In this first window, either the echo spacing TE, or the pulsed field gradient amplitude, or the diffusion time $\Delta$ between the pulsed field gradients is varied, such that the diffusion information of fluids in pore space is encoded. The second window usually is a CPMG pulse sequence with a smallest TE possible to acquire such encoded information. Once the t in the second kernel $k_2(t, TE, D)$ is fixed to be $t_d$, Eq.(6) becomes:

$$b(t, TE) = \int a(T_2) c(D) k_2(t_d, TE, D) k_1(t, T_2) dD dT_2 + \varepsilon \quad (7)$$

where now the two kernels are separated, and the inversion can be easily implemented to obtain a 2D NMR distribution through methods described in U.S. patent applications 20020104326 and 20020067164 and Sun, B. and Dunn, K-J., "Probing the internal field gradients in porous media", Phys. Rev. E 65:051309 (2002).

Thus, two-window type modified CPMG pulse sequences were thought to be essential in separating the two kernels and were necessary for the implementation of an inversion to obtain a 2D NMR display. Such two-window type modified CPMG pulse sequences are undesirable because special NMR tools are required to produce and collect the respective modified CPMG pulse sequences and sequences of echo trains.

Accordingly, there is a need for a method which can use conventional logging or laboratory tools and conventional pulse sequences to acquire properties of fluid containing porous media which can be efficiently inverted to create 2D or multi-dimensional plots of those properties. Ideally, these conventional pulse sequences require only a single window regular CPMG pulse sequence rather than multiple-window type modified CPMG pulse sequences. The present invention provides such an efficient method for determining these properties using regular CPMG pulse sequences and logging or laboratory tools.

SUMMARY OF THE INVENTION

The present invention provides a method for obtaining a multi-dimensional proton density distribution from a system of nuclear spins. In one preferred embodiment, a plurality of nuclear magnetic resonance (NMR) data is acquired from a fluid containing porous medium having a system of nuclear spins. An inversion is performed on the plurality of nuclear magnetic resonance data using an inversion algorithm to solve a mathematical problem employing a single composite kernel to arrive at a multi-dimensional proton density distribution. Ideally, the mathematical problem can be cast in the form of a Fredholm integral of the first kind wherein two or more kernels can be reduced to a single composite kernel for ease of solution.

Conventional logging tools and regular CPMG pulse sequences can be used to obtain a plurality of NMR data when the distribution of proton density is to be obtained in terms of $T_2$ relaxation times and diffusion coefficients D.

Alternatively, proton density as a distribution of $T_2$ relaxation times and internal field gradients g can also be obtained using only conventional CPMG pulses sequences.

The present invention also provides a method of performing a global inversion on a set of echo trains. More details regarding the particular variables and indices to use in this method will be described below. The echo trains are ideally first obtained using regular CPMG pulse sequences. The CPMG echo data is compressed into a column data vector $\{\tilde{b}_r\}$ of length $$N_w = \sum_{k=1}^{q} w_k$$

where there are a total of q echo trains and the k-th echo train with $TE_k$ is compressed to $w_k$ data bins, and $r=1, \ldots, N_w$. A matrix problem $\tilde{b}_r = \tilde{E}_{r,ij} f_{ij} + \epsilon_r$ is set up to obtain a 2D distribution $f_{ij}$. A predetermined number of p diffusion coefficients and m $T_2$ relaxation times are chosen and are ideally equally spaced on corresponding logarithmic scales to form a 2D grid of dimensions p×m and an E matrix of dimension $N_w \times (p \times m)$. The distribution is preferably solved using a least squares minimization algorithm subject to non-negativity constraint at each grid point to obtain a solution vector $f_{ij}$ having a length of p×m.

Small values for p and m may be selected to form an initial coarse grid. These values of p and m are selected such that they are not smaller than the degrees of freedom of the system which is determined by the most significant singular values of the E matrix. This procedure projects the data vector into the subspace associated with the most significant singular values. The distribution is then solved for that coarse grid to determine the values of the proton density distribution at each grid point. Grid points having non-zero values are retained as are their neighboring grid points while the rest of the grid points are eliminated. The retained grid points are then replaced with a finer grid and solved to create a new distribution. The steps of calculating grid points with non-zero values and retaining those grid points and their neighbors and replacing them with a finer grid and solving to create a new distribution are repeated until a solution for the distribution has reached a desired resolution.

It is an object of the present invention to determine 2D NMR data from echo trains obtained using inexpensive, conventional logging tools and NMR apparatus.

It is another object to apply conventional or regular CPMG pulse sequences, having differing echo spacings and/or wait times, to a fluid containing porous media to create sequences of echo trains which are subsequently inverted into a 2D NMR proton distribution using a global inversion algorithm.

It is another object to use a global inversion algorithm, which solves a Fredholm integral of the first kind with a tensor product of two kernels which may have a tangled together common variable, to invert conventional CPMG data (echo trains) into information needed to create 2D NMR displays.

BRIEF DESCRIPTION OF THE DRAWINGS

These and other objects, features and advantages of the present invention will become better understood with regard to the following description, pending claims and accompanying drawings where:

BEST MODE(S) FOR CARRYING OUT THE INVENTION

Figure 1A:
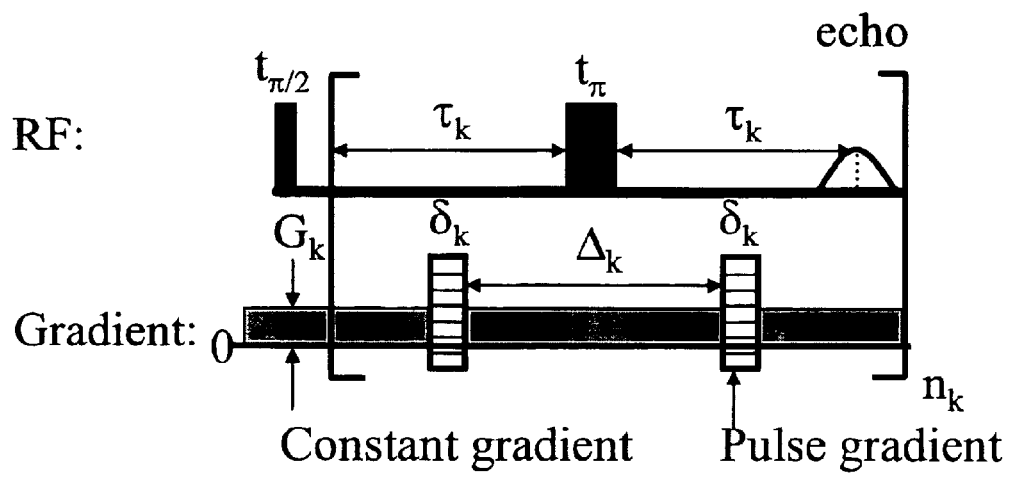
FIGS. 1A and 1B are schematic drawings of a regular CPMG pulse sequence and CPMG echo train.
Figure 1B:
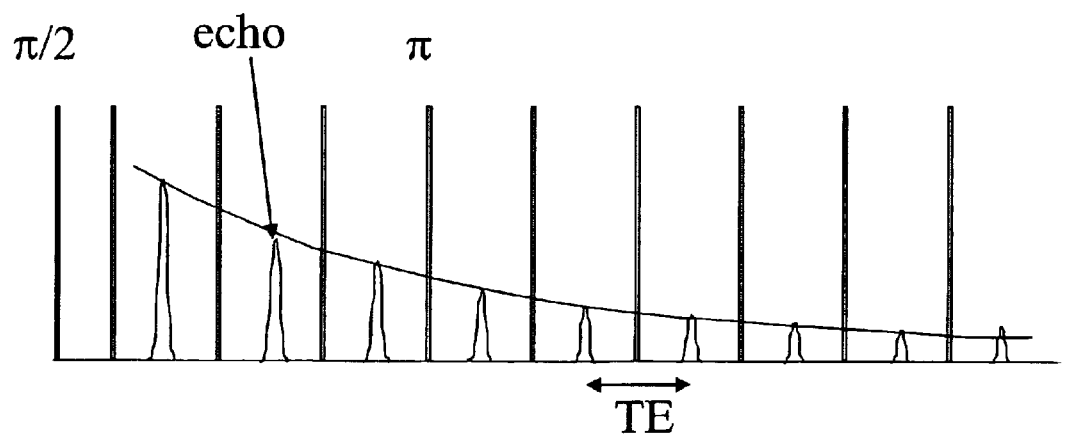
Figure 2A:
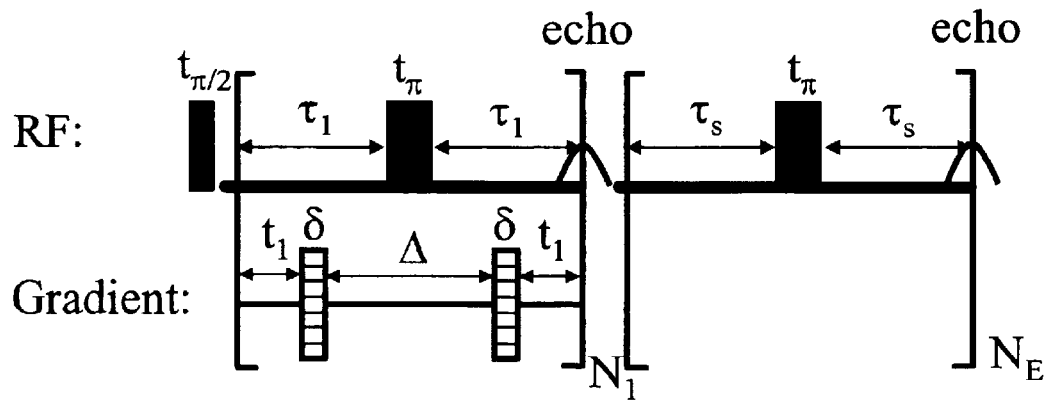
FIGS. 2A and 2B illustrate a single pulse sequence and a series of pulse sequences, each of which utilize a first window and a second window to produce decoupled echo trains which can be inverted, using a prior art multi-step inversion algorithm, to obtain information necessary to produce a 2-dimensional plot.
Figure 2B:
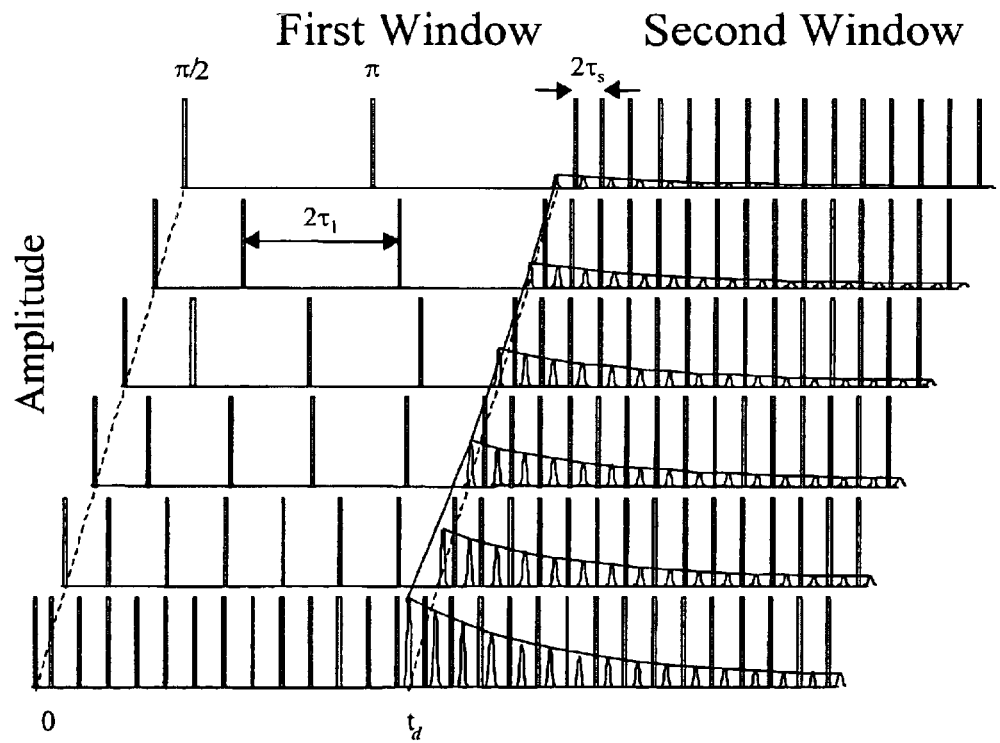
Figure 3:
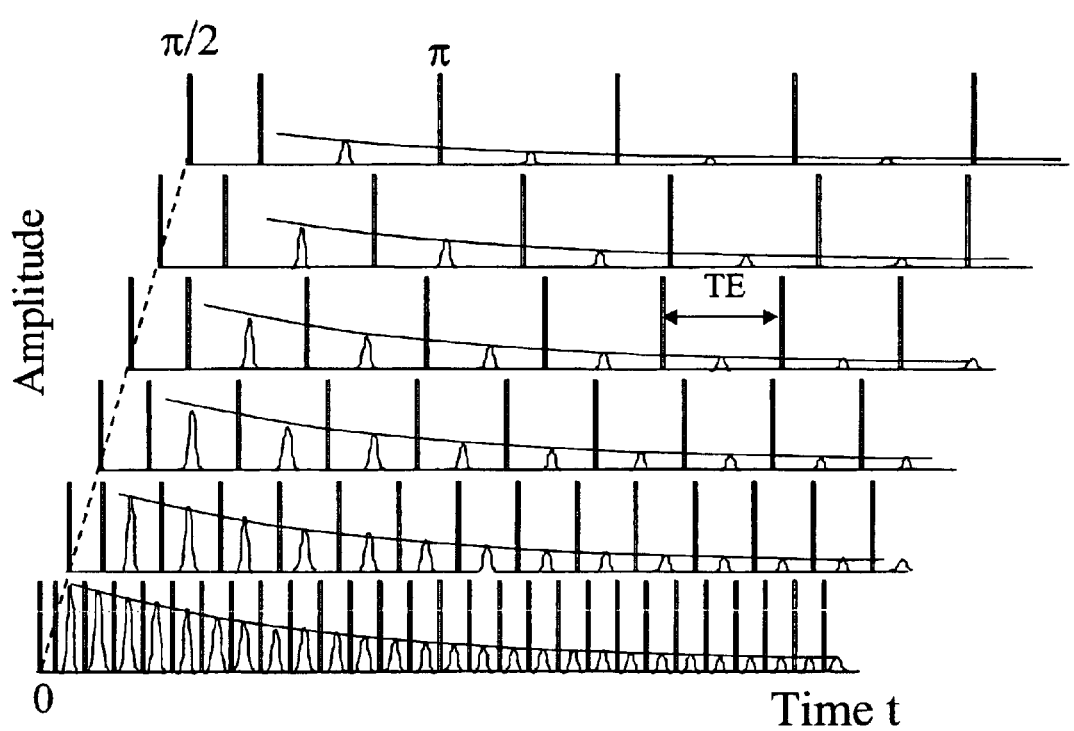
FIG. 3 illustrates a preferred embodiment of a plurality of regular CPMG pulse sequences, having differing echo spacings TE between pulses sequences, which can be used with a global inversion algorithm of the present invention to obtain information necessary to produce a multi-dimensional plot of NMR results.

The present invention provides a method for obtaining a multi-dimensional proton density distribution from a fluid containing porous medium. A plurality of pulse sequences are applied to the fluid containing porous medium to create a plurality of echo train data of a particular character. This character allows the plurality of echo train data to be inverted by a novel inversion algorithm which comports with solving a Fredholm integral of the first kind utilizing a single composite kernel to arrive at a multi-dimensional proton density distribution.

If a multi-dimensional proton density distribution is to be determined with respect to $T_2$ relaxation times and diffusion coefficients D using the inversion algorithm of the present invention, the plurality of pulse sequences may be regular CPMG pulse sequences wherein each pulse sequence has a different echo spacing. A user may specify the $T_2$ relaxation times and diffusion coefficients for which the density distribution is to be solved. Similarly, a multi-dimensional proton density distribution can be solved for in terms of selected $T_2$ relaxation times and gradient g. The particular method of the present invention also readily allows a multi-dimensional proton density distribution to be solved in terms of longitudinal relaxation times $T_1$ and transverse relaxation times $T_2$, however using a different series of pulses to excite a set of nuclear spins.

This novel inversion method shows that separation of kernels is not necessary for obtaining a multi-dimensional proton density distribution. No two-window type modified CPMG pulse sequences are needed. The input data can be a set of regular CPMG echo trains with different echo spacings and/or wait-times acquired by a commercial logging tool or a laboratory NMR spectrometer.

Theoretical Background

Note that without a two-window type modified CPMG pulse sequences, a regular CPMG pulse sequences with a set of different echo spacing times TE would give Eq. (6):

$$b(t,TE) = \int a(T_2) c(D) k_2(t,TE,D) k_1(t,T_2) dD dT_2 + \epsilon. \quad (6)$$

In the present invention, this problem is cast in a two-dimensional framework with a single composite kernel:

$$b(t,TE) = \int f(D,T_2) k(t,TE,D,T_2) dD dT_2 + \epsilon. \quad (8)$$

In discrete form, Eq. (8) can be written as:

$$b_{ik} = \sum_{j=1}^{m} \sum_{l=1}^{p} f_{lj} \exp\left(-\frac{1}{12} \gamma^2 g^2 TE_k^2 D_l t_i\right) \exp(-t_i/T_{2j}) + \varepsilon_{ik}, \quad (9)$$

where $b_{ik}$ is the amplitude of i-th echo using $TE_k$, and $\epsilon_{ik}$ represents noise associated with the nuclear magnetic resonance data. There are m $T_2$ relaxation times and p diffusion coefficients assumed by a model for which the proton density distribution is to be solved. Ideally both $T_2$ relaxation times and p diffusion coefficients are equally spaced on their respective logarithmic scales. Thus, to write Eq. (9) in simplified notation, we have:

$$b_{ik} = f_{lj} E_{ik,lj} + \epsilon_{ik}, \quad (10)$$

where i=1, ..., $n_k$, k=1, ... q, l=1, ..., p, j=1, ..., m  (11)

i is the running index for the echoes of the k-th echo train;

k is the running index for the echo trains;

l is the running index for the pre-selected components of diffusion coefficients in the first dimension;

j is the running index for the pre-selected components of relaxation time in the second dimension;

$n_k$ is the number of echoes in the k-th echo train collected;

q is the number of echo trains with different TEs;

p is the number of pre-selected components of diffusion coefficients in the first dimension;

m is the number of pre-selected components of relaxation times in the second dimension;

$b_{ik}$ is the amplitude of i-th echo of the k-th echo train using echo spacing $TE_k$.

$f_{lj}$ is the proton amplitude at diffusion coefficient $D_l$ and relaxation time $T_{2j}$; and $$E_{ik,lj} = \exp(-\tfrac{1}{12} \gamma^2 g^2 TE_k^2 D_l t_i) \exp(-t_i/T_{2j}) \quad (12)$$

$\gamma$ is the gyromagnetic ratio;

g is the magnetic field gradient; and $TE_k$ is the echo spacing of the k-th echo train.

Eq. (10) can be cast in a matrix form as shown in the following and ideally solved by any least squares minimization routines subject to a non-negativity requirement for $f_{lj}$:

$$\begin{bmatrix} b_{11} \\ \vdots \\ b_{n_1 1} \\ b_{12} \\ \vdots \\ b_{n_2 2} \\ \vdots \\ \vdots \\ \vdots \end{bmatrix} = \begin{bmatrix} E_{11,11} & \cdots & E_{11,1m} & E_{11,2m} & \cdots & E_{11pl} & \cdots & E_{11,pm} \\ \vdots & & & & & & & \\ E_{n_1 1,11} & \cdots & & & & & & \\ E_{12,11} & \cdots & & & & & & \\ \vdots & & & & & & & \\ E_{n_2 2,11} & \cdots & & & & & & \\ \vdots & & & & & & & \\ \vdots & & & & & & & \\ \vdots & & & & & & & \end{bmatrix} \begin{bmatrix} f_{11} \\ \vdots \\ f_{1m} \\ f_{21} \\ \vdots \\ f_{2m} \\ \vdots \\ f_{pl} \\ \vdots \\ f_{pm} \end{bmatrix} \quad (13)$$

To solve Eq. (13) in a practical manner, each echo train can be compressed or averaged to several data bins, with the variance of the noise for each data bin properly taken care of as weighting factor for each corresponding data bin. Thus the large number of echoes can be reduced to a manageable number of data bins. The commonly used singular value decomposition (SVD) method (See *Numerical Recipes*, by Press, W. H., Teukolsky, S. A., Vetterling, W. T., and Flannery, B. P., Cambridge Univ. Press (1992)), or the Butler-Reeds-Dawson (BRD) method (Butler, J. P., Reeds, J. A., and Dawson, S. V., "Estimating Solutions of the First Kind Integral Equations With Non-Negative Constraints and Optimal Smoothing," SIAM J. Numer. Anal. 18, 381–397 (1981)), or the combinations thereof, can be used in the usual manner by imposing the non-negativity constraint and ensuring the solution to be commensurate with the noise level. The methods for such an inversion have been discussed extensively in the literature and are well known to those skilled in the NMR arts.

Examples of such discussions include: Silva, M. D., Helmer, K. G., Lee, J-H., Han, S. S., Springer, C. S. Jr., and Sotak, C. H., "Deconvolution of Compartmental Water Diffusion Coefficients in Yeast-Cell Suspension Using Combined $T_1$ and Diffusion Measurements," J. Magn. Reson., 156, 52–63 (2002); Provencher, S. W., "A Constrained Regularization Method For Inverting Data Represented by Linear Algebraic or Integral Equations," Comput. Phys. Commun. 27, 213–227 (1982); Provencher, S. W., "CONTIN: A General Purpose Constrained Regularization Program for Inverting Noisy Linear Algebraic or Integral Equations," Comput. Phys. Commun. 27, 229–242 (1982); Lee, J-H., Labadie, C., Springer, C. S., and Harbison, G. S., "Two Dimensional Inverse Laplace Transform NMR: Altered Relaxation Times Allow Detection of Exchange Correlation," J. Am. Chem. Soc. 115, 7761–7764 (1993); and English, A. E., Whittall, K. P., Joy, M. L. G., and Henkelman, R. M., "Quantitative Two-Dimensional Time Correlation Relaxometry," Magn. Reson. Med. 22, 425–434 (1991).

Suppose that the first echo train, having $n_1$ echoes, is compressed to $w_1$ data bins, and the k-th echo train, having $n_k$ echoes, is compressed to $w_k$ data bins, and so on. These data bins are partitioned equally spaced in a logarithmic time scale. The amplitudes of the echoes within each data bin are averaged to produce an averaged echo amplitude, and this averaged echo amplitude is weighted by multiplying a weighting factor which is equal to the product of the square root of the number of echoes within the data bin and a ratio of the largest noise level of all q echo trains to the noise level of the k-th echo train. The compressed CPMG echo data is arranged to form a column data vector $\{\tilde{b}_r\}$ of length $$N_w = \sum_{k=1}^{q} w_k; \quad (14)$$

where the compressed q echo trains are concatenated sequentially and $r=1, \ldots, N_w$ replacing the indices ik.

Eq. (10) now becomes $$\tilde{b}_r = \tilde{E}_{r,ij} f_{ij} + \epsilon_r \quad (15)$$

where $\tilde{E}$ is a matrix of dimension $N_w \times (p \times m)$ where each row of $\tilde{E}$ is weighted by the same weighting factor of the corresponding row in $\{\tilde{b}_r\}$. When using SVD to solve for Eq. (15), it is required that $N_w \geq p \times m$; whereas using BRD, such requirement is not needed and $N_w < p \times m$ is acceptable.

For example, typically m=15 and p=15 is selected. For a data vector $b_{ik}$ of length $N_w=300$, the dimension of the $\tilde{E}$ matrix will be 300×225. With the current GHz PC, one inversion takes about ten seconds. However, if the grid size is increased to 30×30 with a $N_w \geq 900$, a single inversion will take about 20 minutes. Thus to modestly increase the grid size, and hence the resolution of the distribution, the computation time is significantly increased. To overcome this problem, either one of the following two schemes is used to implement the global inversion algorithm in a very efficient manner, which results in improved computation speed without sacrificing the resolution of the distribution.

The distribution $f_{ij}$ has zero value at many of the grid points. Thus significant computation time is wasted in obtaining these zero values. To speed up the computation, the inversion is performed in steps. A small number of grid points is initially chosen to create a coarse grid. Preferably the coarse grid is to be chosen such that the p and m are not smaller than the degrees of freedom of the system which is determined by the most significant singular values of the $\tilde{E}$ matrix.

In a first scheme, the distribution with this coarse grid is calculated. The grid points where the distribution is nonzero, as well as their neighboring grid points, are retained while the rest of the grid points which have zero value are discarded. This results in a much smaller matrix for $\tilde{E}$ and a shorter vector for $f_{ij}$. A finer grid is then chosen for the new $\tilde{E}$ matrix and the new vector $f_{ij}$. After a few iterations of solving for the distribution and retaining only the non-zero value grids and their neighboring grids, a final solution $f_{ij}$ can be quickly obtained with good resolution. The good resolution may be established by visually inspecting the resulting plot of the density distribution.

In a second scheme, the unitary matrix U derived from the singular value decomposition of the $\tilde{E}$ matrix based on the coarse grid is used to project the data vector as well as a new $\tilde{E}'$ matrix which can be of finer grid to a subspace associated with the most significant singular values. Further minimization of $\hat{b}_r = U^T \tilde{b}_r = U^T \tilde{E}'_{r,ij} f_{ij} + \epsilon_r$ can be accomplished by using BRD method.

Generalization

The global inversion scheme of the present invention can be applied to Fredholm integrals of the first kind where the tensor product of two kernels are tangled together with a common variable as shown in the following:

$$b(t,\tau) = \int \int f(x,y) k_1(t,x) k_2(t,\tau,y) dx dy + \epsilon. \quad (16)$$

In fact, for multiple-fluid-saturated rocks within an internal field gradient distribution, the echo amplitude, or the magnetization of such a system, b, can be cast in a general form as follows which can be obtained with various modified CPMG pulse sequences:

$$b(t,WT,TE) = \int \int \int f(T_1,T_2,D,g) k_1(WT,T_1) k_2(t,T_2) k_3(t,TE,D,g) dg dD dT_1 dT_2 + \epsilon \quad (17)$$

where t is the decay time, WT the wait time between successive CPMG excitations, TE the time between echoes, D the diffusion coefficient, and g the magnetic field gradient. And the kernels are:

$$k_1(WT,T_1) + 1 - \alpha \exp(-WT/T_1), \quad (18)$$

where $\alpha=2$ for the inversion recovery and $\alpha=1$ for the saturation recovery, $$k_2(t,T_2) = \exp(-t/T_2), \quad (19)$$

and $$k_3(t,TE,D,g) = \exp(-\tfrac{1}{12} \gamma^2 g^2 TE^2 Dt). \quad (20)$$

In principle, Eq. (16) can be solved with a single composite kernel which is the product of the three kernels shown above with a matrix form as B=Ax. The dimension of the matrix involved will be prohibitively large. In the following, specific cases for combinations of any two kernels shall be elaborated.

For example, if the 2D NMR display for $T_1$ and $T_2$ is considered, Eq. (17) reduces to:

$$b(t,WT) = \int \int f(T_1,T_2) k_1(WT,T_1) k_2(t,T_2) dT_1 dT_2 + \epsilon. \quad (21)$$

This will be a trivial problem to solve as the two kernels are separable.

For the 2D NMR display for D and $T_2$, or g and $T_2$, Eq. (17) reduces to:

$$b(t,TE) = \int \int f(T_2,D) k_2(t,T_2) k_3(t,TE,D) dD dT_2 + \epsilon \quad (22)$$

or $$b(t,TE) = \int \int f(T_2,g) k_2(t,T_2) k_3(t,TE,g) dg dT_2 + \epsilon \quad (23)$$

where the problem can be solved either by fixing the t in the kernel $k_3$ using two-window type modified CPMG pulse sequences, or by combining the two kernels into a single composite kernel and using Eq. (13).

Those skilled in the art will appreciate there are various other combinations of parameters for 2D, or 3D, or higher dimensional NMR displays which may also be obtained using the principles of the above described invention.

EXAMPLES

Figure 4:
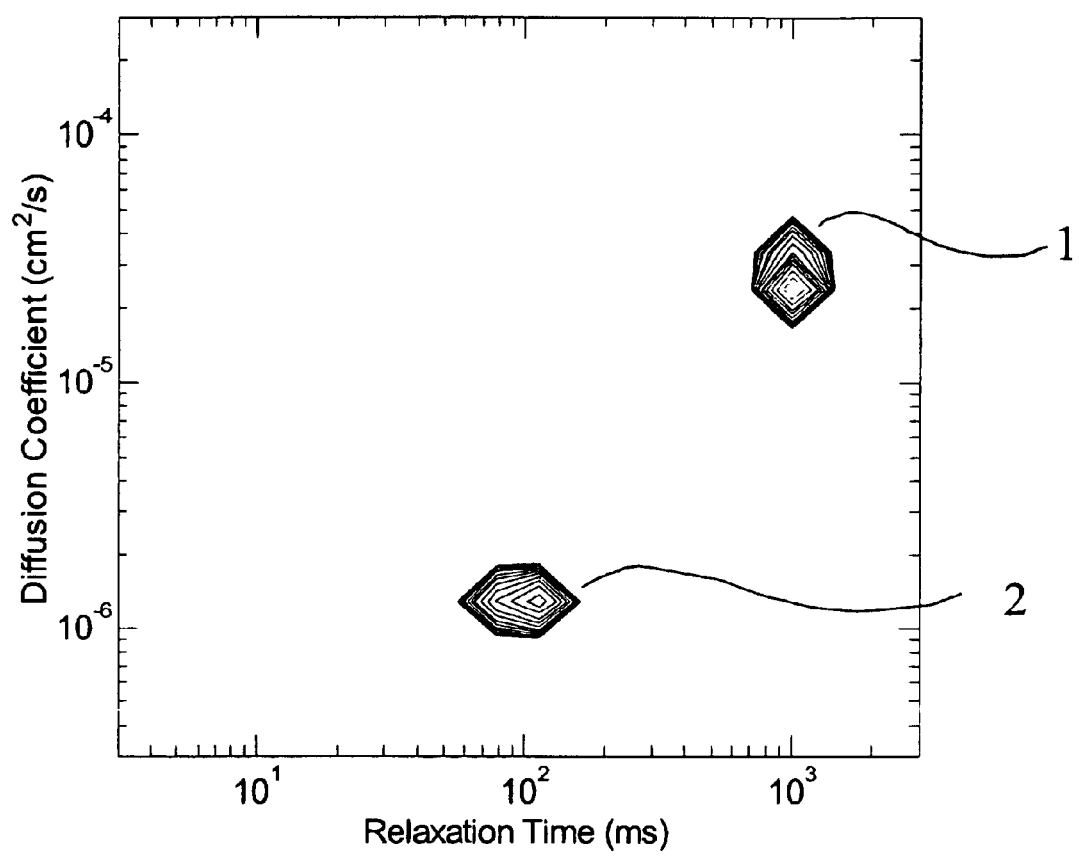
FIG. 4 is a 2D NMR contour plot, made using information obtained in accordance with the present invention, of diffusion coefficients D and $T_2$ relaxation times versus proton amplitude.

Example 1: FIG. 4

To verify the concepts described in the above description, simulated regular CPMG echo trains have been used as input data and then the Global Inversion for Relaxation-Diffusion 2D NMR (GIRD) algorithm described above is used to obtain the Relaxation-Diffusion 2D NMR (RD2D) distribution. The GIRD result is shown in FIG. 4 which is a contour plot of RD2D distribution, showing the fluid #1 on top and fluid #2 at the bottom correctly recovering their respective value of diffusion coefficient.

In the simulation, the $T_2$ relaxation time of a fluid #1 is set to be 1 second and of a second fluid #2 to be 100 ms. The diffusion coefficient D of fluid #1 is $2.5 \times 10^{-5}$ cm$^2$/s and fluid #2 is $10^{-6}$ cm$^2$/s. The population of fluid #1 is 60 pu and of fluid #2 is 40 pu. The noise level is 1 pu. Fifteen TE values were used with minimum TE of 0.2 ms and maximum TE of 20 ms. Twenty relaxation components were used with $T_2$ minimum of 3 ms and maximum of 3 s. The number of different diffusion coefficients was also set to 20 with D minimum of $3 \times 10^{-7}$ cm$^2$/s and maximum of $3 \times 10^{-4}$ cm$^2$/s. The gradient G used in the simulation was 10 gauss/cm.

Figure 5:
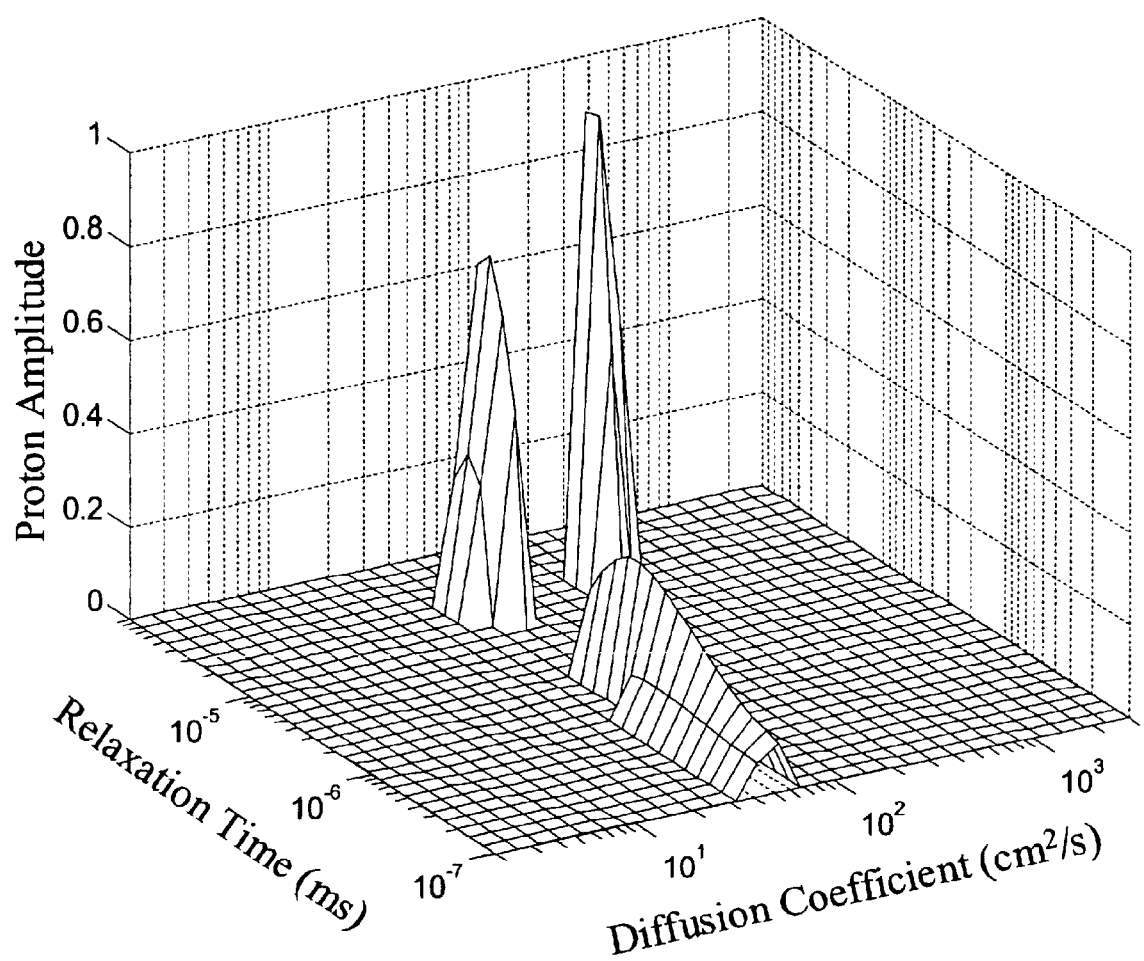
FIG. 5 is a 2D NMR plot, in three dimensions, of diffusion coefficients D along a first axis, $T_2$ relaxation times along a second axis and proton amplitudes along a third axis.

Example 2: FIG. 5

This example is also a simulation result: the $T_2$ relaxation, for water is set at 300 ms and 50 ms, each with 30 pu, and for oil at 50 ms with 40 pu. A set of 10 echo trains with varying TE was generated with a Gaussian white noise of 1 p.u. The diffusion coefficients D for water and oil have the same values as used in Example 1 as is the magnetic field gradient G. Note that the recovered values for $T_2$ and D through the GIRD algorithm are quite close to the original values. The assumed 2D map has a dimension of 25×25 with diffusion coefficient values varying from $10^{-7}$ to $10^{-3}$ cm$^2$/s and $T_2$ relaxation times from 1 to $10^4$ ms.

Figure 6:
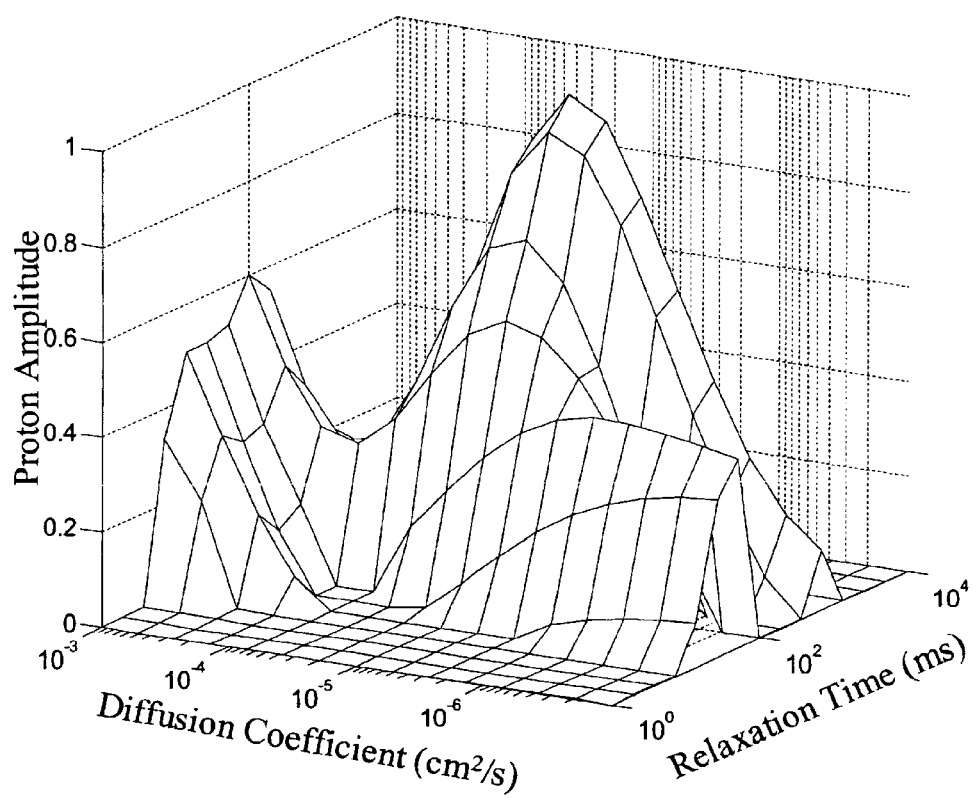
FIG. 6 is a 2D NMR plot, in three dimensions, of diffusion coefficients D along a first axis, $T_2$ relaxation times along a second axis and proton amplitudes along a third axis.

Example 3: FIG. 6

Example 3, shown in FIG. 6, was produced from actual NMR log data: A set of four echo trains with TE values of 0.2, 2, 4, and 6 ms were obtained. This 2D map has a range for D and $T_2$ which is the same as that for Example 2, except a coarser grid size, 15×15, was used. Vendor's gradient field map was built in for the inversion. This 2D map shows that the right hand side peak is an oil bump and to the left is a water bump. The apparent diffusion coefficient of water is almost an order of magnitude higher than what it should be expected due to the strong internal magnetic field gradients in the pore space. The low diffusion coefficient value was not well resolved due to the lack of data for large TE. The largest TE in the simulation for Example 2 was 51.2 ms, whereas for this example the largest TE was only 6 ms.

Figure 7:
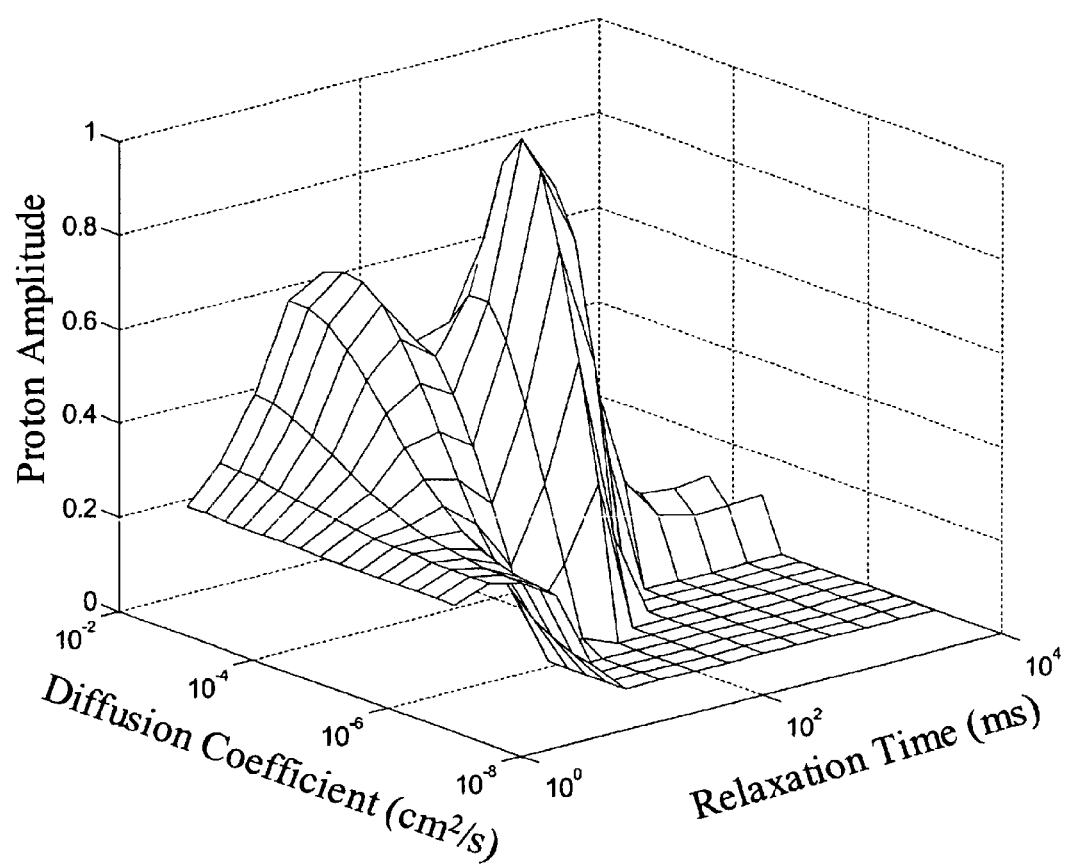
FIG. 7 is a 2D NMR plot, in three dimensions, of diffusion coefficients D along a first axis, $T_2$ relaxation times along a second axis and proton amplitudes along a third axis.

Example 4: FIG. 7

FIG. 7 was produced from real NMR log data as well. The log data was acquired with the same conditions and the data was analyzed in the same manner as the data in Example 3. This depth interval contains heavy oil, and part of the signal was not recovered by NMR log measurements.

While in the foregoing specification this invention has been described in relation to certain preferred embodiments thereof, and many details have been set forth for purpose of illustration, it will be apparent to those skilled in the art that the invention is susceptible to alteration and that certain other details described herein can vary considerably without departing from the basic principles of the invention.

What is claimed is:

1. A method for obtaining a multi-dimensional proton density distribution from a system of nuclear spins, the method comprising:

a) acquiring a plurality of nuclear magnetic resonance (NMR) data with a series of regular CPMG pulse sequences from a fluid containing porous medium having a system of nuclear spins; and b) performing an inversion on the plurality of nuclear magnetic resonance data without separating or untangling the NMR data by using an inversion algorithm to solve a mathematical problem employing a single composite kernel and thereby arrive at a multi-dimensional proton density distribution.

2. The method of claim 1 wherein:

the mathematical problem conforms to a Fredholm integral of the first kind and the single composite kernel is a combination of a plurality of kernels.

3. The method of claim 2 wherein:

the Fredholm integral of the first kind may be expressed in the following mathematical form $$b(t,TE,G) = \int \int f(T_2,D) k_2(t,T_2) k_3(t,TE,G,D) dD dT_2 + \epsilon$$

where b(t,TE,G) represents the nuclear magnetic resonance data where t is the decay time, TE is the time between two successive echoes, and G is the external applied magnetic field gradient;

$f(T_2,D)$ represents the multi-dimensional proton density distribution to be solved in terms of relaxation time $T_2$ and D;

$k_2(t,T_2)$ represents a kernel which is a function of decay time t and transverse relaxation time $T_2$;

$k_3(t,TE,G,D)$ represents a kernel which is a function of decay time t, the time between two successive echoes TE, G is the external applied magnetic field gradient;

$\epsilon$ represents noise level; and the composite single kernel is a combination of two tangled kernels of the form $k_2(t,T_2)$ and $k_3(t,TE,G,D)$.

4. The method of claim 2 wherein:

the Fredholm integral of the first kind may be expressed in the following mathematical form $$b(t,TE,G) = \int \int f(T_2,g) k_2(t,T_2) k_3(t,TE,g) dg dT_2 + \epsilon$$

wherein where b(t,TE,G) represents the nuclear magnetic resonance data where t is the decay time, TE is the time between two successive echoes, and G is the external applied magnetic field gradient;

$f(T_2,g)$ represents the multi-dimensional proton density distribution to be solved in terms of relaxation time $T_2$ and the total magnetic field gradient g;

$k_2(t,T_2)$ represents a kernel which is a function of decay time t and transverse relaxation time $T_2$;

$k_3(t,TE,g)$ represents a kernel which is a function of decay time t, the time between two successive echoes TE, and the total magnetic field gradient g;

$\epsilon$ represents noise level; and the single composite kernel is a combination of two tangled kernels of the form $k_2(t,T_2)$ and $k_3(t,TE,g)$.

5. The method of claim 2 wherein:

the Fredholm integral of the first kind may be expressed in the following mathematical form $$b(t,WT) = \int \int f(T_1,T_2) k_1(WT,T_1) k_2(t,T_2) dT_1 dT_2 + \epsilon$$

where b(t,WT) represents the nuclear magnetic resonance data where t is the decay time and WT is the wait time between successive pulses;

$f(T_1,T_2)$ represents the multi-dimensional proton density distribution to be solved in terms of longitudinal relaxation time $T_1$ and transverse relaxation time $T_2$;

$k_1$ (WT,$T_1$) represents a kernel which is a function of wait time WT and longitudinal relaxation time $T_1$;

$k_2$(t,$T_2$) represents a kernel which is a function of decay time t and transverse relaxation time $T_2$;

$\epsilon$ represents noise level; and the single composite kernel is a combination of two untangled kernels of the form $k_1$(WT,$T_1$) and $k_2$(t,$T_2$).

6. The method of claim 1 wherein:

the system of spins is excited by a plurality of pulse sequences which are characterized by at least one of t,WT,TE,G,$\Delta$,$\delta$ where t is the decay time, WT is the wait time between two successive pulse sequences, TE is the time between two successive echoes, G is the external applied magnetic field gradient, $\Delta$ is the diffusion time between pulsed field gradient, $\delta$ is the width of pulsed field gradient; and the mathematical problem comports with the general expression $$b(t,WT,TE,G,\Delta,\delta)=\int\int\int\int f(T_1,T_2,D,g)k_1(WT,T_1)k_2(t,T_2)k_3(t,TE,\Delta,\delta,D,g)dgdDdT_1dT_2+\epsilon$$

where b(t,WT,TE,G,$\Delta$,$\delta$) represents the nuclear magnetic resonance data, f($T_1$,$T_2$,D,g) represents a multi-dimensional distribution to be extracted from the system of nuclear spins, $T_1$ represents longitudinal relaxation time, $T_2$ represents transverse relaxation time, D represents diffusion coefficient, and g is the total magnetic field gradient;

$k_1$(WT,$T_1$) represents a first kernel dependent upon wait time WT and longitudinal relaxation time $T_1$;

$k_2$(t,$T_2$) represents a second kernel dependent upon decay time t and transverse relaxation time $T_2$;

$k_3$ (t,TE,$\Delta$,$\delta$,D,g) represents a third kernel dependent upon decay time t, echo spacing TE, diffusion time $\Delta$, width of pulsed field gradient $\delta$, and total magnetic field gradient g, and $\epsilon$ represents noise level.

7. The method of claim 1 wherein:

the mathematical problem comports with the general expression $$b(t,\tau)=\int f(x,y)k_1(t,x)k_2(t,\tau,y)dxdy+\epsilon;$$

where b(t,$\tau$) represents the nuclear magnetic resonance data for a particular decay time t and half echo spacing $\tau$;

f(x,y) is a multi-dimensional proton density distribution of x and y which represent parameters related to the system of spins;

$k_1$ (t,x) is a first kernel;

$k_2$(t,$\tau$,y) is a second kernel;

$\epsilon$ represents noise associated with the nuclear magnetic resonance data; and wherein the first and second kernels are tangled with respect to particular decay time t.

8. The method of claim 1 wherein: the step of acquiring a plurality of nuclear magnetic resonance (NMR) data includes applying a plurality of RF pulse sequences to the fluid containing porous medium, each RF pulse sequence having a single window.

9. The method of claim 1 wherein:

the step of acquiring a plurality of nuclear magnetic resonance (NMR) data includes applying a plurality of RF pulse sequences, each RF pulse sequence being a regular CPMG pulse sequence comporting to the following expression:

$$\left(\frac{\pi}{2}\right)_{\pm x}[-\tau_k-\pi_y-\tau_k-acq-]_{n_k}$$

where $$\left(\frac{\pi}{2}\right)$$

is 90 degree pulse applied along the plus and minus x-axis with respect to a reference in the rotating frame;

$\tau_k$ is half of the echo spacing $TE_k$ of the k-th echo train;

$\pi_y$ is a 180 degree pulse applied along y axis in the rotating frame:

acq represents an acquisition of an echo; and $n_k$ is the number of echoes in the k-th echo train.

10. The method of claim 1 wherein: the mathematical problem comports to meet the general expression $$b_{ik}=f_{lj}E_{ik,\,lj}+\epsilon_{ik},$$

where i=1, ..., $n_k$, k=1, ..., q, l=1, ..., p, j=1, ..., m i is the running index for the echoes of the k-th echo train;

k is the running index for the echo trains;

l is the running index for the pre-selected components of diffusion coefficients in the first dimension;

j is the running index for the pre-selected components of relaxation time in the second dimension;

$n_k$ is the number of echoes in the k-th echo train collected;

q is the number of echo trains with different TEs;

p is the number of pre-selected components of diffusion coefficients in the first dimension;

m is the number of pre-selected components of relaxation times in the second dimension;

$b_{ik}$ is the amplitude of i-th echo of the k-th echo train using echo spacing $TE_k$ $f_{lj}$ is the proton amplitude at diffusion coefficient $D_l$ and relaxation time $T_{2j}$; and $$E_{ik,lj}=\exp\left(-\frac{1}{12}\gamma^2g^2TE_k^2D_lt_i\right)\exp(-t_i/T_{2j})$$

$\gamma$ is the gyromagnetic ratio;

g is the magnetic field gradient; and $TE_k$ is the echo spacing of the k-th echo train.

11. The method of claim 1 wherein:

the single composite kernel includes tangled variables.

12. An NMR method of obtaining a multi-dimensional proton density distribution from a fluid containing porous medium, the method comprising;

applying a plurality of regular CPMG pulse sequences to a fluid containing porous medium;

obtaining a plurality of regular CPMG echo trains from the fluid containing porous medium; and inverting the regular CPMG echo trains using an inversion algorithm without separating or untangling the regular CPMG echo trains and thereby obtaining a multi-dimensional proton density distribution.

13. The method of claim 12 wherein:

the inversion algorithm includes solving a Fredholm integral of the first kind.

14. The method of claim 12 wherein:

the CPMG pulse sequences are applied in accordance with the expression $$\left(\frac{\pi}{2}\right)_{\pm x} [-\tau_k - \pi_y - \tau_k - acq-]_{n_k}$$

where $$\left(\frac{\pi}{2}\right)$$

is 90 degree pulse applied along the plus and minus x-axis with respect to a reference in the rotating frame;

$\tau_k$ is halt of the echo spacing $TE_k$ of the k-th echo train;

$\pi_y$ is a 180 degree pulse applied along y axis in the rotating frame;

acq represents an acquisition of an echo; and $n_k$ is the number of echoes in the k-th echo train.

15. The method of claim 12 wherein:

the inversion algorithm solves the general expression $$b_{ik} = f_{lj} E_{ik,lj} + \epsilon_{ik},$$

where i=1, ..., $n_k$, k=1, ..., q, l=1, ..., p, j=1, ..., m i is the running index for the echoes of the k-th echo train;

k is the running index for the echo trains;

l is the running index for the pre-selected components of diffusion coefficients in the first dimension;

j is the running index for the pre-selected components of relaxation time in the second dimension;

$n_k$ is the number of echoes in the k-th echo train collected;

q is the number of echo trains with different TEs;

p is the number of pre-selected components of diffusion coefficients in the first dimension;

m is the number of pre-selected components of relaxation times in the second dimension;

$b_{ik}$ is the amplitude of i-th echo of the k-th echo train using echo spacing $TE_k$ $f_{lj}$ is the proton amplitude at diffusion coefficient $D_l$ and relaxation time $T_{2j}$; and $$E_{ik,lj} = \exp\left(-\frac{1}{12}\gamma^2 g^2 TE_k^2 D_l t_i\right) \exp(-t_i/T_{2j})$$

$\gamma$ is the gyromagnetic ratio;

g is the magnetic field gradient; and $TE_k$ is the echo spacing of the k-th echo train.

16. The method of claim 12 wherein:

the plurality of pulse sequences include at least one differentiating variable which is differentiated between the plurality of pulse sequences.

17. The method of claim 16 wherein:

the differentiating variable is one of Time between Echoes (TE), wait time (WT) between pulse sequences, and magnetic gradient field g is the magnetic field gradient.

18. The method of claim 16 wherein:

the differentiating variable is Time between Echoes (TE).

19. A method of performing a global inversion on a set of NMR echo trains, which solves a Fredholm integral of the first kind with a tensor product of two kernels which may have a tangled together common variable, to invert conventional CPMG data (NMR echo trains) into information needed to create 2D NMR display, the method comprising:

(a) capturing a set of regular CPMG echo trains which comport with the following expression $$b_{ik} = f_{lj} E_{ik,lj} + \epsilon_{ik},$$

where i=1, ..., $n_k$, k=1, ..., q, l=1, ..., p, j=1, ..., m i is the running index for the echoes of the k-th echo train;

k is the running index for the echo trains;

l is the running index for the pre-selected components of diffusion coefficients in the first dimension;

j is the running index for the pre-selected components of relaxation time in the second dimension;

$n_k$ is the number of echoes in the k-th echo train collected;

q is the number of echo trains with different TEs;

p is the number of pre-selected components of diffusion coefficients in the first dimension;

m is the number of pre-selected components of relaxation times in the second dimension;

$b_{ik}$ is the amplitude of i-th echo of the k-th echo train using echo spacing $TE_k$ $f_{lk}$ is the proton amplitude at diffusion coefficient $D_l$ and relaxation time $T_{2j}$; and $$E_{ik,lj} = \exp\left(-\frac{1}{12}\gamma^2 g^2 TE_k^2 D_l t_i\right) \exp(-t_i/T_{2j})$$

$\gamma$ is the gyromagnetic ratio;

g is the magnetic field gradient; and $TE_k$ is the echo spacing of the k-th echo train;

(b) compressing the regular CPMG echo data, $\{b_{ik}\}$, to a column data vector $\{\tilde{b}_r\}$ of length $$N_w = \sum_{k=1}^{q} w_k$$

where there are a total of q echo trains and the k-th echo train with $TE_k$ is compressed to $w_k$ data bins, and r=1, ..., $N_{wi}$ (c) setting up the matrix problem $\tilde{b}_r = \tilde{E}_{r,lj} f_{lj} + \epsilon_r$ to obtain the 2D distribution $f_{lj}$;

(d) choosing p diffusion coefficients and m $T_2$ relaxation times each equally spaced on corresponding logarithmic scales to form a 2D grid of dimensions p×m and an E matrix of dimension $N_w \times (p \times m)$; and (e) solving the distribution by least squares minimization algorithm subject to non-negativity constraint at each grid point to obtain a solution vector $f_{lj}$ having a length of p×m.

20. The step of claim 19 further comprising:

(f) selecting small values for p and m to form a coarse grid and solving the distribution to determine the values of the distribution at each grid point;

(g) retaining the grid points having non-zero values and their neighboring grids and eliminating the rest of the grid points;

(h) replacing the retained grid points with a finer grid and solving for a new distribution; and (i) repeating steps (g) and (h) until the final solution has been achieved a satisfactory resolution.

21. The step of claim 19 further comprising:
(j) selecting small values for p and m to form a coarse grid, wherein the coarse grid is to be chosen such that the p and m are not smaller than the degrees of freedom of the system which is determined by the most significant singular values of the $\tilde{E}$ matrix;
(k) deriving a unitary matrix U from the singular value decomposition of the $\tilde{E}$ matrix based on the coarse grid;
(l) projecting the data vector as well as a new $\tilde{E}'$ matrix which can be of a finer grid to a subspace associated with the most significant singular values; and
(m) minimizing $\tilde{b}_r = U^T \tilde{b}_r = U^T \tilde{E}'_{r,ij} f_{ij} + \epsilon_r$ using BRD method.

* * * * *